United States Patent [19]

Chandra et al.

[11] Patent Number: 4,673,733

[45] Date of Patent: Jun. 16, 1987

[54] TREATMENT OF BIOLOGICAL AND PHARMACEUTICAL PRODUCTS ADSORBED ON A SOLID PHASE WITH VIRUS AND PYROGEN INACTIVATING AGENTS

[76] Inventors: Sudhish Chandra, 884 S. McKinley Ave., Kankakee, Ill. 60901; Fred Feldman, 407 Gettysburg, Park Forest, Ill. 60466

[21] Appl. No.: 722,561

[22] Filed: Apr. 11, 1985

[51] Int. Cl.[4] .......................... A61K 35/14; C07G 7/06
[52] U.S. Cl. ..................................... 530/344; 530/383; 530/412; 530/413; 530/415; 210/656; 210/927; 424/101; 435/803; 435/815
[58] Field of Search ............... 260/112 B, 112 R, 122; 435/803, 815; 210/656, 660, 927; 424/79, 101; 530/344, 412, 413, 415, 383

[56] References Cited

U.S. PATENT DOCUMENTS

| | | | |
|---|---|---|---|
| 4,105,598 | 8/1978 | Yen et al. | 260/112 B |
| 4,147,592 | 4/1979 | Bai et al. | 435/215 |
| 4,315,919 | 2/1982 | Shanbrom | 424/101 |
| 4,321,363 | 3/1982 | Takiguchi et al. | 435/215 |
| 4,380,511 | 4/1983 | Mannuzzo et al. | 260/112 B |
| 4,511,556 | 4/1985 | Purcell et al. | 424/89 |

Primary Examiner—Harold D. Anderson
Assistant Examiner—Nathan M. Nutter

[57] ABSTRACT

A method for treating a biological or pharmaceutical product to inactivate viruses and pyrogens therein comprising the steps of adsorbing said product onto a solid phase; treating the adsorbed product with a virus or pyrogen inactivating agent; separating the solid phase and quantitatively removing the residual inactivating agent therefrom; and recovering said product.

28 Claims, No Drawings

TREATMENT OF BIOLOGICAL AND PHARMACEUTICAL PRODUCTS ADSORBED ON A SOLID PHASE WITH VIRUS AND PYROGEN INACTIVATING AGENTS

BACKGROUND OF THE INVENTION

1. Field of the Invention

This invention relates to a method of reducing the pyrogenicity and infectivity of hepatitis B or other viruses in biological and pharmaceutical products. More particularly this invention relates to a method of inactivating viruses and pyrogens which contaminate biological and pharmaceutical products by adsorbing said products on a solid phase and subjecting them to a treatment with an agent which inactivates viruses and/or pyrogens.

2. Description of the Prior Art

It is well-known that biological and pharmaceutical products may contain transmissible biological contaminants, such as viruses, and especially infectious hepatitis viruses, such as hepatitis virus B, and non-A, non-B hepatitis viruses. Contamination by viruses may result from both the source material used and from the environment during their production.

Pyrogens are lipopolysaccharides also known as endotoxins, having numerous biologic activities which include the production of fever, activation of clotting mechanisms and induction of shock. Consequently, it is essential that pyrogenic substances be removed from products intended for biological or pharmaceutical use.

Methods for inactivation or destruction of viruses and/or pyrogens include treatment with heat, acid or alkali, filtration, removal by adsorption with gels, ion-exchange resin and various other such adsorbent material. Most of these methods are burdensome, time consuming, or destructive of the product due to the rigorousness of the treatment.

Simple treatment with virus or pyrogen inactivating agents like Triton, Tween, beta-propiolactone or hypochlorite may result in inactivation of the viruses and/or pyrogenic materials but is accompanied by partial denaturation of labile proteins. Even if the proteins are not denatured, the quantitative removal of the residual virus inactivating agent or pyrogen inactivating agent may be very difficult and its contamination makes the biological or pharmaceutical product undesirable.

Illustrative of the use of virus and/or pyrogen inactivating agents is U.S. Pat. No. 4,314,997 which discloses the use of amphiphiles to destroy endotoxin and to inactivate hepatitis viruses in plasma derivatives by direct contact of the amphiphiles with the plasma derivatives in solution. After treatment, the plasma proteins are separated from the amphiphiles by precipitation. Such separation may not completely remove the inactivating agents from the precipitated protein and the final product, therefore, may contain pharmaceutically harmful and/or undesirable inactivating agents.

It is, therefore, the principal object of the present invention to provide a method to substantially inactivate viruses and pyrogens in biological and pharmaceutical products.

It is another object of the present invention to completely remove the inactivating agents from the product treated to provide a pharmaceutically acceptable end product.

These and further objects as shall hereinafter appear are achieved by the present invention in a remarkable unexpected fashion as will be discerned from the following description.

SUMMARY OF THE INVENTION

It has now been discovered that viruses and pyrogens may be inactivated in biological or pharmaceutical products by a method comprising the steps of:
   adsorbing said product onto a solid phase;
   treating the solid phase adsorbed product by contacting the same with a virus inactivating or depyrogenating agent;
   separating the product bound solid phase from the virus inactivating or depyrogenating agent;
   washing the solid phase to remove the residual virus inactivating or depyrogenating agent; and
   recovering the product by elution from the solid phase.

DETAILED DESCRIPTION OF THE INVENTION

The process of the present invention is applicable to any material in the biomedical field intended to be used in the human or animal body for biomedical or therapeutic purposes as well as non-therapeutic experimental purposes. Contemplated biomedical products and materials which can be depyrogenated or made free of viruses using the process of the present invention include but are not limited to:

blood fractions such as antihemophilic factor A (AHF, Factor VIII), prothrombin complex (Factors II, VII, IX and X), individual or group of Factor II, Factor VII, Factor IX, Factor X, Protein C, Antithrombin III, C-1 Esterase Inhibitor, Fibronectin, Gamma Globulin, and Albumin derived from human or animal origin; biological and pharmaceutical products derived from animal origin, e.g. insulin, enzymes, coenzymes, antibodies, and hormones; and biological products derived from human or animal placentae, e.g., blood fractions, and vaccines.

These products and materials are available from various commercial sources or can be produced by using well-known preparative techniques. For example, blood fractions and blood proteins can be obtained from human blood plasma by fractionation according to known techniques such as, for example, the alcohol fractionation method of Cohn described in U.S. Pat. No. 2,390,074 and the Journal of the American Chemical Society Vol. 68, p. 459 (1946). These methods as well as other techniques are summarized in "The Plasma Proteins", second edition, Volume III, pp. 548–550, Academic Press, New York, N.Y. (1977).

As used herein, the "solid phase" on which said biological or pharmaceutical product is adsorbed is meant to define a substance used as ion exchanger, resins used for affinity chromatography, resins with an attached antibody against the particular or related antigen, special membrane media which act as an ion exchanger or are capable of adsorbing particular substances, or glass beads which are treated to produce surfaces that act as an ion exchanger or affinity resin. Contemplated solid phase materials include:

a, An ion exchanger, e.g., DEAE Sephadex, QAE Sephadex, CM-Sephadex, SP-Sephadex, DEAE Biogel A, CM Biogel A, Biogel HTP, DEAE Cellulose;

b, Resins used for affinity chomatography, such as Sepharose 2B, Sepharose 4B, Sepharose 6B, Sepharose CL-2B, Sepharose CL-4B and Biogel A-15 with an attached ligand consisting of, for example, an inhibitor, enzyme, coenzyme, or hormone. The attached ligand is capable of adsorbing the biological or pharmaceutical product, for example, heparin attached to a sepharose resin adsorbs Antithrombin III. The attached ligand may be an antibody to the antigen or related antigen present in the product. An example is antibody to Anti-hemophilic Factor related antigen attached to a Sepharose resin to adsorb Antihemophilic Factor. The attached ligand may also be a monoclonal or polyclonal antibody to the antigen which might be desired to be isolated as the biological or pharmaceutical product;

c, Resins described in b above with an attached antibody (monoclonal or polyclonal) against a particular antigen or an antigen itself;

d, Special membrane media which act as an ion exchanger, e.g., Zeta-Prep ™ cartridge, DEAE, QAE, and SP;

e, Controlled-Pore Glass beads which are treated to produce surfaces that act as an ion exchanger, e.g., DEAE-CPG, CML-CPG; and f, Controlled-Pore Glass beads attached with biologicals of interest such as inhibitors, enzymes, coenzymes, hormones, antibodies, and antigens.

The virus inactivating and depyrogenating agents used in the present invention are the amphiphiles, organic solvents, hypoclorite or beta propiolactone.

The term amphiphile means a substance containing both hydrophilic water soluble and hydrophobic water-insoluble groups and which are generally classified as cationic, anionic, ampholytic and non-ionic surface active agents.

Agents of the cationic type include long chain amine condensates with ethylene oxide and quaternary ammonium compounds, for example cetyl trimethyl ammonium bromide and dodecyl dimethyl ammonium bromide. Suitable anionic agents include soaps, salts of aliphatic monoesters of sulphuric acid, for example sodium lauryl sulphate and sodium heptadecyl sulphate, sulphonated aromatic compounds, for example alkyl benzene sulphonic acids and salts thereof such as tridecylbenzene sulphonic acid and the sodium and amino salts of dodecylbenzene sulphonic acid, alkyl napthalene sulphonates such as sodium butylnapthalene sulphonate, sulphosuccinates such as sodium dioctyl sulphosuccinate, and N-acyl-N-alkyl fatty acid taurates.

Non-ionic agents include (a) ethoxylated alkylphenols (b) ethoxylated aliphatic alcohols, (c) carboxylic esters and (d) carboxylic amides, as described hereinafter (a) The ethoxylated alkylphenol non-ionic surface active agents include various polyethylene oxide condensates of alkylphenols, especially the condensation products of mono-alkylphenols or di-alkylphenols wherein the alkyl group contains about 6 to about 12 carbon atoms in either branched chain or particularly straight chain configuration, for example octyl cresol, octyl phenol or nonyl phenol, with ethylene oxide, the said ethylene oxide being present in amounts equal to from about 5 to about 25 moles of ethylene oxide per mole of alkylphenol.

(b) One particular type of ethoxylated aliphatic alcohol non-ionic surface active agents is the condensation products of aliphatic alcohols having from about 8 to 18 carbon atoms in either straight chain or branched chain configuration, for example oleyl or cetyl alcohol, with ethylene oxide, the said ethylene oxide being present in equal amounts of from about 30 to about 60 moles of ethylene oxide per mole of alcohol.

(c) Particular types of carboxylic ester non-ionic surface active agents are firstly the partial, for example mono-esters formed by the reaction of fatty and resin acids, for example of about 8 to about 18 carbon atoms with polyhydric alcohols, for example glycerol, glycols such as mono-, di-, tetra- and hexaethylene glycol, sorbitan, etc; and similar compounds formed by the direct addition of varying molar ratios of ethylene oxide to the hydroxy group of fatty acids.

A second type of carboxylic esters is the condensation products of fatty and resin acid partial, for example monoesters with ethylene oxide, such as fatty or resin acid esters of polyoxyethylene sorbitan and sorbitol, for example polyoxyethylene sorbitan mono-tall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow whilst examples of single fatty acids are dodecanoic acid and oleic acid.

(d) One particular type of carboxylic amide non-ionic surface active agents is the ammonia, monoethanol and diethanol amides of fatty acids having an acyl chain of from about 8 to about 18 carbon atoms.

The ampholitic agents include dodecyl-alanine, N-dodecylaminoethanesulfonic acid, palmitoyl-lysolecithin and dodecyl-N-betaine.

Organic solvents which may be used for the process of the present invention include dimethyl ether, diethyl ether, ethyl propyl ether, methyl-butyl ether, methyl isopropyl ether, methyl isobutyl ether, chloroform, methanol, ethanol, propanol, isopropanol, n-butanol, isobutanol, n-pentanol and ispentanols.

Referring now specifically to the process steps of the present invention, the product to be treated is first adsorbed onto the solid phase, followed by subjecting the so-adsorbed product to the virus or pyrogen inactivating agent in a liquid or gas phase for sufficient time to complete inactivation and depyrogenation therein. The virus or pyrogen inactivating agent is generally present in amounts of from 0.1% to 50%, preferably from 0.5% to 20%, and most preferably of from 1% to 10% based on the volume of the product. If the inactivating agent is in the liquid phase, the pH of the solution should be from about 5 to 9 and preferably from about 6 to 8. The time necessary to complete inactivation generally is from 2 minutes to 16 hours, more preferably from 1 to 10 hours. The process of inactivation may be performed at a temperature ranging from 0° C. to 50° C.; if the inactivating agents used are gaseous, the temperature range is generally lower, while liquid phase inactivating agents are employed at or close to room temperature. The inactivating agent in gaseous form can be used as such or as an aerosol spray to treat the solid phase adsorbed product.

Preferably, the treatment of the biomedical or pharmaceutical product adsorbed on a solid phase is carried out with the virus or pyrogen inactivating agent, by treating the solid phase adsorbed product with a buffer solution containing an inactivating agent. The treatment is carried out in a column operation or batchwise by immersing or soaking the solid phase in the buffer solution containing the inactivating agent. Suitable buffer solutions include: phosphate, citrate, tris aminomethane, glycine or any other buffering agent which does not adversely interact with the biological or pharmaceutical material being processed.

Upon completing the inactivation step, the inactivating agent is removed by separating the liquid or gas phase from the solid phase. The liquid phase can be separated by the use of a column, by centrifuging or by filtration.

Upon completing the separation, the solid phase is washed extensively with a solution of buffer used in the previous step of inactivation, said buffer having an ionic strength of 0.05M to 2.0M, and preferably 0.10M to 0.25M, and a pH of from about 5 to 9, and preferably from about 6 to 8. The washing is to remove impurities adsorbed on the solid phase and to remove the agent used to depyrogenate or inactivate the virus. This is preferably accomplished in a column or batchwise operation. While a solution of the same buffering agent is preferred to remove impurities and quantitatively remove the inactivating agent, other solutions such as phosphate, citrate, tris, glycine or any buffering agent which does not interact with the biological or pharmaceutical material and has similar ionic strength may also be used.

The pure biological or pharmaceutical product is then eluted from the solid phase with a buffer solution of phosphate, citrate, tris aminomethane, glycine or any other buffering agent which does not adversely interact with the biological or pharmaceutical material being processed and has an ionic strength of 0.15M to 3.5M, and preferably from 0.5M to 2.5M, and a pH of from about 5 to 9, and preferably from about 6 to 8. Other solutions of sodium chloride, calcium chloride, magnesium chloride, epsilon amino caproic acid, or sodium citrate in a buffer described above may also be used for eluting the pure product.

In order to more fully illustrate the nature of the invention and the manner of practicing the same, the following examples are presented:

EXAMPLE 1

Human plasma fraction, cryopoor plasma, used for Prothrombin Complex isolation, is adsorbed on DEAE-Sephadex A-50 (Pharmacia). The ion exchanger with Prothrombin Complex proteins adsorbed on it is then treated with Triton X-100 radio labelled with Triton (2% Triton X-100 containing $^3H$ radio labelled Triton X-100 which gives a total of 167,340 counts per minute). Triton X-100 solution is then separated by filtration and the DEAE-Sephadex is washed three times with a buffer solution (0.01M sodium citrate, 0.2M sodium chloride, pH 7.0). During these washings all the Triton X-100 is washed off. Thereafter, Prothrombin Complex is eluted by a buffer of higher ionic strength (0.01M sodium citrate, 2.0M sodium chloride, pH 7.0). This eluate is found to be free of Triton X-100 as shown in Table I. (As seen in Table I, more than 99.99% of the agent is removed.) Thus the agent used to inactivate viruses or pyrogens is quantitatively removed and the final product is free of the agent.

TABLE I

| | TOTAL CPM | % OF ORIGINAL RADIOACTIVITY |
|---|---|---|
| TRITON X-100 CONTAINING $^3H$ TRITON X-100 ADDED DURING 1ST WASH | 167,340,000 | 100 |
| 1ST WASH | 162,470,000 | |
| 2ND WASH | 4,350,500 | 99.93 |
| 3RD WASH | 507,500 | |
| ELUATE | 11,640 | 0.0069 |

EXAMPLE 2

Plasma fraction used for Prothrombin Complex isolation (plasma from which cryoprecipitate was removed) is spiked with Sindbis or Vesicular Stomatitis virus (VSV). It is then adsorbed on DEAE-Sephadex and treated with 2% Triton X-100 solution for 30 minutes to inactivate the virus. The ion exchanger is then separated from Triton X-100 solution by filtration and washed three times with a buffer consisting of 0.01M sodium citrate and 0.2M sodium chloride, at pH 7.0, to wash off residual Triton X-100 and impurities bound to DEAE-Sephadex non-specifically. The Prothrombin Complex is eluted by a buffer of higher ionic strength (2M sodium chloride, 0.01M sodium citrate, at pH 7.0), diafiltered, and ultrafiltered to physiological conditions. As control, experiments are repeated after spiking the plasma fractions with the respective virus. However, treatment of Prothrombin Complex after adsorption on DEAE-Sephadex with 2% Triton X-100 is omitted in the control experiment.

The final Prothrombin Complex, the starting plasma fractions, and intermediate fractions were assayed for virus activity by a method similar to that described by E. R. Pfefferkon and H. S. Hunter (Virology 20, 433-445, 1963), and briefly summarized hereunder.

Chick embryo fibroblasts (CEF) were seeded into 100mm plastic dishes and allowed to grow to confluence (48 hours). Serial tenfold dilutions of samples were made in minimal essential medium (MEM) containing 10% fetal calf serum and 1.0 ml inoculated onto replicate plates from which culture medium had previously been drained. The plates were incubated for one hour at 37° C. in 5% $CO_2$ after which the inoculum was aspirated and 10 ml per plate of overlay medium added. The overlay medium consisted of MEM with 10% heat inactivated fetal calf serum and 1% agarose. The overlay was allowed to solidify after which cultures were incubated at 37° C. in 5% $CO_2$ for about 24 hours. At this time, cytopathology was evident in positive cultures. A 0.002% solution of neutral red in phosphate buffered saline was then added, and cultures were incubated an additional four hours. After this period, plaques were counted and virus activity was represented in terms of plaque forming units (PFU).

Tables II and III show that by treatment with Triton X-100, using the method described in this invention, virus activities of Sindbis and VSV are reduced $2.07\times10^3$ and $8.45\times10^4$ fold respectively as compared to control experiments.

TABLE II

SINDBIS INACTIVATION DURING PURIFICATION AND DETERGENT TREATMENT

| | TRITON TREATMENT | | | CONTROL | | |
|---|---|---|---|---|---|---|
| | | VIRUS AMOUNT | | | VIRUS AMOUNT | |
| | VOL-ML | PFU/ML | TOTAL PFU | VOL-ML | PFU/ML | TOTAL PFU |
| STARTING PLASMA FRACTION | 10,000 | $7.76 \times 10^6$ | $7.76 \times 10^{10}$ | 10,000 | $1.15 \times 10^7$ | $1.15 \times 10^{11}$ |
| DEAE-UNADSORBED | 10,000 | $6.10 \times 10^6$ | $6.10 \times 10^{10}$ | 10,000 | $5.95 \times 10^6$ | $5.95 \times 10^{10}$ |
| WASH-(TRITON) | 500 | — | — | — | — | — |
| WASH - 1 | 3,340 | $3.90 \times 10^2$ | $1.30 \times 10^6$ | 3,340 | $5.83 \times 10^5$ | $1.95 \times 10^8$ |
| WASH - 2 | 3,340 | — | — | 3,340 | — | — |
| WASH - 3 | 3,340 | — | — | 3,340 | — | — |
| ELUATE | 200 | $9.83 \times 10^2$ | $1.97 \times 10^5$ | 220 | $6.83 \times 10^6$ | $1.50 \times 10^9$ |
| PROTHROMBIN COMPLEX BULK AFTER UF/DF | 152 | $2.24 \times 10^3$ | $3.40 \times 10^5$ | 201 | $5.22 \times 10^6$ | $1.04 \times 10^9$ |
| REDUCTION IN VIRUS | $2.28 \times 10^5$ FOLD | | | $1.10 \times 10^2$ FOLD | | |
| REDUCTION AS COMPARED TO CONTROL | $2.07 \times 10^3$ FOLD | | | | | |

TABLE III

VSV INACTIVATION DURING PURIFICATION AND DETERGENT TREATMENT

| | TRITON TREATMENT | | | CONTROL | | |
|---|---|---|---|---|---|---|
| | | VIRUS AMOUNT | | | VIRUS AMOUNT | |
| | VOL-ML | PFU/ML | TOTAL PFU | VOL-ML | PFU/ML | TOTAL PFU |
| STARTING PLASMA FRACTION | 10,000 | $5.0 \times 10^3$ | $5.0 \times 10^7$ | 10,000 | $4.5 \times 10^3$ | $4.5 \times 10^7$ |
| DEAE-UNADSORBED | 10,000 | $1.5 \times 10^3$ | $1.5 \times 10^7$ | 10,000 | $3.0 \times 10^3$ | $3.0 \times 10^7$ |
| WASH (TRITON) | 500 | — | — | — | — | — |
| WASH - 1 | 3,340 | — | — | 3,340 | $4.0 \times 10^2$ | $1.36 \times 10^6$ |
| WASH - 2 | 3,340 | — | — | 3,340 | — | — |
| WASH - 3 | 3,340 | — | — | 3,340 | — | — |
| ELUATE | 300 | $<0.25$ | $<7.5 \times 10^1$ | 300 | $1.93 \times 10^4$ | $5.79 \times 10^6$ |
| PROTHROMBIN COMPLEX BULK AFTER UF/DF | 216 | $<0.25$ | $<5.4 \times 10^1$ | 212 | $2.91 \times 10^4$ | $6.17 \times 10^6$ |
| REDUCTION IN VIRUS | $>9.3 \times 10^5$ FOLD | | | 11 FOLD | | |
| REDUCTION AS COMPARED TO CONTROL | $>8.45 \times 10^4$ FOLD | | | | | |

EXAMPLE 3

250 ml cryopoor plasma is spiked with endotoxin to obtain a concentration of 100 ng/ml. The spiked plasma is then stirred with 4 g. of preswollen DEAE-Sephadex to adsorb Prothrombin Complex factors including Factor IX on the resin. The resin is then treated with 2% Triton X-100 solution in 0.01M sodium citrate, 0.2M sodium chloride at pH 7.0 to depyrogenate. Thereafter, the resin is washed three times with aliquots of 85 ml solution of 0.01M sodium citrate, 0.2M sodium chloride at pH 7.0. Factor IX is then eluted from the resin by a solution of 0.01M sodium citrate, 2M sodium chloride at pH 7.0, dialyzed, and ultrafiltered against 0.13M sodium chloride, 0.01M sodium citrate at pH 7.0 to a volume of 5 ml. In control experiment treatment of factor IX after adsorption on DEAE-Sephadex with Triton X-100 is omitted.

The final Prothrombin Complex concentrates thus obtained are assayed for Factor IX potency, clotting factors' activation, and endotoxin. Factor IX is assayed using a slight modification of the one stage method of Barrow & Graham (In Tocantins and Kazal, Blood Coagulation, Hemorrhage and Thrombosis, Grune and Stratton, New York 1964 p. 120), activation measured by the Nonactivated Partial Thromboplastin Time Test (NAPTT) of Kingdon and coworkers (Thromb. Diath. Haemorrh. 33, 617–631, 1975) and endotoxin by a modification of LAL test described by Levin and coworkers (Ann. Intern. Med. 76:1, 1972).

Results presented in Table IV show that treatment with 2% Triton X-100 using the method of this invention results in practically no impact on Factor IX potency, Prothrombin Complex factors remain in zymogen form (non-activated), and the level of endotoxin is reduced by 70 ng/ml.

TABLE IV

| | PROTHROMBIN COMPLEX CONCENTRATE | |
|---|---|---|
| TEST | CONTROL | TRITON X-100 TREATED |
| FACTOR IX U/ML | 23.2 | 21.6 |
| NAPTT | Negative | Negative |
| LAL NG/ML | 80 | 10 |

Examples 1–3 show that by the use of DEAE-Sephadex resin as a solid phase and Triton X-100 as virus inactivating or depyrogenating agent, proteins of Prothrombin Complex, e.g., Factor IX, are depyrogenated and depleted of virus contamination and the end product results in having no residual amounts of Triton X-100.

EXAMPLE 4

Depyrogenation of Plasminogen by Treatment with Triton X-100 on Lysine-Sapharose Solid Phase Plasma is spiked with endotoxin at a final concentration of 20 ng/ml, then it is applied on a column consisting of Lysine-Sepharose resin. Plasminogen is adsorbed to the column. In the column, resin is then treated with 2% Triton X-100 to depyrogenate it. Residual Triton is then removed by washing with 0.3M phosphate buffer at pH 7.3, and plasminogen is eluted by a solution of 0.2M epsilon amino caproic acid in 0.05M phosphate buffer at pH 7.3. Finally, the eluate is dialyzed against phosphate buffered saline solution at pH 7.3, and a purified preparation of plasminogen with less than 0.1 ng endotoxin per ml is obtained.

EXAMPLE 5

Inactivation of Vesicular Stomatitis Virus (a marker) During Isolation of Antithrombin III by Treatment on Heparin-Sepharose, Solid Phase Heparin attached to Sepharose is packed in a column. Cryopoor plasma is spiked with VSV to a titer of $5 \times 10^6$ total PFU and passed through this column. Antithrombin III is adsorbed on the solid phase, which is then treated with 2% Triton X-100 in phosphate buffered saline to inactivate the virus. The column is then washed extensively with 0.5M sodium chloride in phosphate buffer, at pH 7.3, to remove residual Triton X-100 and the impurities bound nonspecifically to the solid phase. Thereafter, Antithrombin III is eluted by 2M sodium chloride in phosphate buffer at pH 7.3. The Antithrombin III is then dialyzed against phosphate buffered saline at pH 7.3 to obtain a final purified Antithrombin III preparation in which the virus was reduced to less than 0.25 PFU/ml.

EXAMPLE 6

Inactivation of Viruses at the Solid Phase Consisting of Monoclonal Antibody Against Factor VIII:R Ligand Attached to Sepharose During Isolation of Factor VIII Monoclonal antibody against Factor VIII:R Ag is attached to sepharose resin, and packed in a column. A suspension of cryoprecipitate is spiked with VSV, as a controlled experiment, to a concentration of approximately $5 \times 10^7$ PFU. It is then passed through the column where Factor VIII molecules (which consist of subunits of Factor VIII:C Antigen and Factor VIII:R Antigen) adsorb through the Factor VIII:R Antigen portion of the molecule. The resin is then treated with 2% Tween 80 solution in a wash buffer consisting of 100mM lysine, 20 mM histidine, 0.15M sodium chloride, at pH 7.0, to inactivate the virus. Residual Tween 80 is removed by an extensive washing of the column using the above wash buffer. The Factor VIII:C portion of the Factor VIII molecule is then desorbed by an elution buffer consisting of 0.25M calcium chloride in the wash buffer. Once Factor VIII:C antigen is desorbed, remaining Factor VIII:R antigen is also desorbed by 3M sodium thiocyanate in the above wash buffer. Both Factor VIII:C and Factor VIII:R solutions are separately concentrated and dialyzed against normal physiological saline to obtain Factor VIII:C (clotting) and Factor VIII:R (von Willebrand) preparations practically free of virus, i.e., less that 0.25 PFU/ml.

EXAMPLE 7

Isolation of Protein C Free of Viruses by Treatment with Triton X-100 at a Solid Phase Consisting of Pore Glass CPG-DEAE Cryopoor plasma spiked with a marker virus, e.g., VSV, to a concentration of $5 \times 10^6$ total PFU is passed through a column packed with CPG-DEAE. Protein C is adsorbed on the column which is then treated with 2% Triton X-100 in the wash buffer, 0.01M sodium citrate, 0.2M sodium chloride, at pH 7.0, to inactivate the marker virus. Residual Triton X-100 and other impurities are removed by washing the column extensively with wash buffer. Protein C is then eluted from the column by 0.25M sodium citrate, 0.55M sodium chloride at pH 6.0. The eluate is then dialyzed against normal physiological saline solution and a Protein C preparation free of marker virus, VSV, (less than 0.25 PFU/ml) is obtained.

Various modifications will be apparent to the person skilled in the art after reading the present disclosure without departing from the spirit and scope of the invention; it is intended that all such modifications be included within the scope of the appended claims.

What is claimed is:

1. A method to depyrogenate or inactivate viruses in a biological or pharmaceutical product comprising the steps of:
    adsorbing said product onto a solid phase;
    contacting said product adsorbed on said solid phase with a virus inactivating or depyrogenating agent;
    separating the solid phase from the virus inactivating or depyrogenating agent;
    removing impurities and residual inactivating or depyrogenating agent from the solid phase; and
    recovering the product from the solid phase.

2. The method of claim 1 wherein said solid phase is an ion exchanger resin.

3. The method of claim 1 wherein said solid phase is an affinity resin having attached thereto a ligand capable of adsorbing biological or pharmaceutical products.

4. The method of claim 3 wherein said ligand is selected from the group consisting of an inhibitor, enzyme, coenzyme or hormone.

5. The method of claim 4 wherein said ligand is heparin.

6. The method of claim 1 wherein said solid phase is an affinity resin having attached thereto a monoclonal or polyclonal antibody.

7. The method of claim 6 wherein said antibody is antibody to Antihemophilic Factor antigen.

8. The method of claim 1 wherein said solid phase is controlled-pore glass beads adapted to produce ion exchange or affinity effect.

9. The method of claim 8 wherein said controlled-pore glass beads are treated with an agent capable of adsorbing biological or pharmaceutical products, said agent is selected from the group consisting of an inhibitor, enzyme, coenzyme, hormone, antibody or antigen.

10. The method of claim 1 wherein said solid phase is a synthetic membrane adapted to produce ion exchange or affinity effect.

11. The method of claim 10 wherein said synthetic membrane is treated with an agent capable of adsorbing biological or pharmaceutical products, said agent is selected from the group consisting of an inhibitor, enzyme, coenzyme, hormone, antibody or antigen.

12. The method of claim 1 wherein said virus inactivating or depyrogenating agent is selected from the group consisting of an amphiphile, organic solvent, hypochlorite, beta propiolactone or mixtures thereof.

13. The method of claim 12 wherein said amphilphile is anionic, cationic, ampholytic or nonionic.

14. The method of claim 12 wherein said organic solvent is selected from the group consisting of dimethyl ether, diethyl ether, ethyl propyl ether, methyl butyl-ether, methyl isopropyl ether, methyl isobutyl ether, chloroform, methanol, ethanol, propanol, butanol, or pentanol.

15. The method of claim 1 wherein said virus inactivating or depyrogenating agent is in a liquid form.

16. The method of claim 1 wherein said virus inactivating or depyrogenating agent is in a buffer solution, said buffer solution containing a buffering agent selected from the group consisting of citrate, phosphate, borate, acetate, bicarbonate, succinate, maleate, phthalate, imidazole, trisamino methane, glycine, lysine, histidine, and mixtures thereof.

17. The method of claim 16 wherein said buffer solution is at a pH of 5 to 9.

18. The method of claim 16 wherein said buffer solution has an ionic strength of 0.05 to 2.0M.

19. The method of claim 1 wherein said virus inactivating or depyrogenating agent is in a gaseous form.

20. The method of claim 1 wherein the separating of the solid phase from the virus inactivating or depyrogenating agent is by filtration.

21. The method of claim 1 wherein the separating of the solid phase from the virus inactivating or depyrogenating agent is by centrifugation.

22. The method of claim 1 wherein the separating of the solid phase from the virus inactivating or depyrogenating agent is by a column.

23. The method of claim 1 wherein said removing of inpurities and residual inactivating or depyrogenating agent is by washing said solid phase with a buffer solution, said buffer solution containing a buffering agent selected from the group consisting of citrate, phosphate, borate, acetate, bicarbonate, succinate, maleate, phthalate, imidazole, trisamino methane, glycine, lysine, or histidine, said buffer solution having a pH of 5 to 9 and an ionic strength of 0.05 to 2.0M.

24. The method of claim 1 wherein said recovering the product from said solid phase is by elution with a buffer solution or desorbing agent, said buffering solution containing a buffering agent selected from the group consisting of citrate, phosphate borate, acetate, bicarbonate, succinate, maleate, phthalate, imidazole, trisamino methane, glycine, lysine, histidine, and the desorbing agent from the group consisting of sodium chloride, calcium chloride, magnesium chloride, epsilon amino caproic acid or sodium citrate and mixtures thereof, said buffer solution having a pH of 5 to 9 and an ionic strength of 0.15 to 3.5M.

25. The method of claim 1 wherein said biological or pharmaceutical product is a plasma protein.

26. The method of claim 1 wherein said biological or pharmaceutical product is derived from human or animal placentae.

27. The method of claim 1 wherein said biological or pharmaceutical product is an enzyme, coenzyme, hormone or insulin.

28. The method of claim 1 wherein said biological or pharmaceutical product is prepared by recombinant DNA or gene splicing technique.

* * * * *